United States Patent
Kennefick et al.

(10) Patent No.: US 6,840,943 B2
(45) Date of Patent: Jan. 11, 2005

(54) INSTRUMENT AND METHOD FOR APPLYING SURGICAL FASTENERS

(75) Inventors: William Kennefick, Plymouth, MA (US); Laurel Rogers, N. Attleboro, MA (US); Christopher McDowell, Raynham, MA (US)

(73) Assignee: Codman & Shurtleff, Inc, Raynham, MA (US)

( * ) Notice: Subject to any disclaimer, the term of this patent is extended or adjusted under 35 U.S.C. 154(b) by 357 days.

(21) Appl. No.: 09/961,198

(22) Filed: Sep. 21, 2001

(65) Prior Publication Data

US 2002/0052607 A1 May 2, 2002

Related U.S. Application Data

(60) Provisional application No. 60/234,491, filed on Sep. 22, 2000.

(51) Int. Cl.[7] .............................................. A61B 17/58
(52) U.S. Cl. ...................................................... 606/104
(58) Field of Search ................................ 606/104, 139, 606/142; 81/463; 29/525.03; 227/147, 132, 175.1, 177.1, 179.1, 901; 72/453.17, 453.19, 466.4, 466.5

(56) References Cited

U.S. PATENT DOCUMENTS

| | | | | |
|---|---|---|---|---|
| 2,839,754 A | * | 6/1958 | Pfaff ........................... 606/104 |
| 3,210,832 A | * | 10/1965 | Kalen ......................... 606/104 |
| 4,263,903 A | * | 4/1981 | Griggs ....................... 128/92 B |
| 4,590,928 A | | 5/1986 | Hunt et al. |
| 4,899,743 A | | 2/1990 | Nicholson et al. |
| 5,290,281 A | | 3/1994 | Tschakaloff |
| 5,290,297 A | | 3/1994 | Phillips |
| 5,398,861 A | | 3/1995 | Green |
| 5,601,558 A | | 2/1997 | Torrie et al. |
| 5,628,857 A | | 5/1997 | Baerveldt |
| 5,641,501 A | | 6/1997 | Cooper et al. |
| 5,643,321 A | | 7/1997 | McDevitt |
| 5,649,931 A | * | 7/1997 | Bryant et al. ............... 606/104 |
| 5,649,963 A | | 7/1997 | McDevitt |
| 5,667,513 A | * | 9/1997 | Torrie et al. ................ 606/104 |
| 5,705,181 A | | 1/1998 | Cooper et al. |
| 5,720,753 A | | 2/1998 | Sander et al. |
| 5,725,529 A | | 3/1998 | Nicholson et al. |
| 5,735,855 A | | 4/1998 | Bradley |
| 5,741,268 A | | 4/1998 | Schutz |
| 5,797,963 A | | 8/1998 | McDevitt |
| 5,814,071 A | | 9/1998 | McDevitt et al. |
| 5,911,721 A | | 6/1999 | Nicholson et al. |
| 5,921,456 A | * | 7/1999 | Kirsch et al. ............... 227/147 |
| 5,928,244 A | | 7/1999 | Tovey et al. |
| 5,947,970 A | | 9/1999 | Schmelzeisen et al. |
| 5,957,927 A | | 9/1999 | Magee et al. |
| 5,957,953 A | * | 9/1999 | DiPoto et al. .............. 606/232 |
| 5,968,044 A | | 10/1999 | Nicholson et al. |
| 5,980,558 A | * | 11/1999 | Wiley ......................... 606/232 |
| 6,033,430 A | | 3/2000 | Bonutti |
| 6,036,073 A | * | 3/2000 | Newhouse .................. 227/147 |
| 6,077,266 A | | 6/2000 | Medoff |
| 6,080,161 A | | 6/2000 | Eaves, III et al. |
| 6,110,178 A | | 8/2000 | Zech et al. |
| 6,189,422 B1 | * | 2/2001 | Stihl ............................ 81/452 |
| 6,241,732 B1 | | 6/2001 | Overaker et al. |
| 6,273,893 B1 | * | 8/2001 | McAllen, III et al. ...... 606/104 |
| 6,319,258 B1 | | 11/2001 | McAllen, III et al. |

FOREIGN PATENT DOCUMENTS

EP            998878 A1      5/2000

* cited by examiner

Primary Examiner—Eduardo C. Robert

(57) ABSTRACT

An instrument for applying fasteners such as bioabsorbable skull rivets, having a piston coaxially received within a housing. The piston has a tip at its distal end and the housing has a distal end sized to receive the tip and also to receive a portion of on of the fasteners. A slit in the housing allows it to flex and accommodate the fastener.

8 Claims, 8 Drawing Sheets

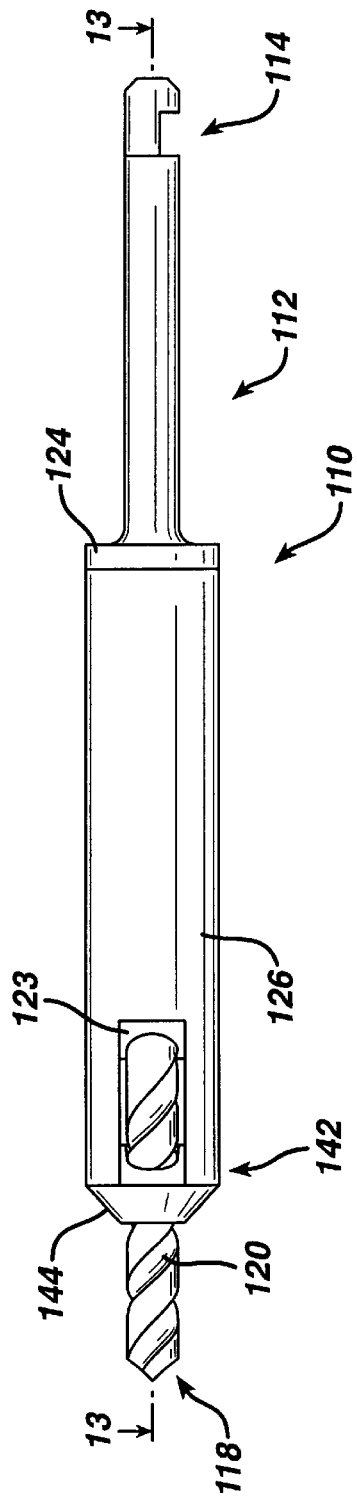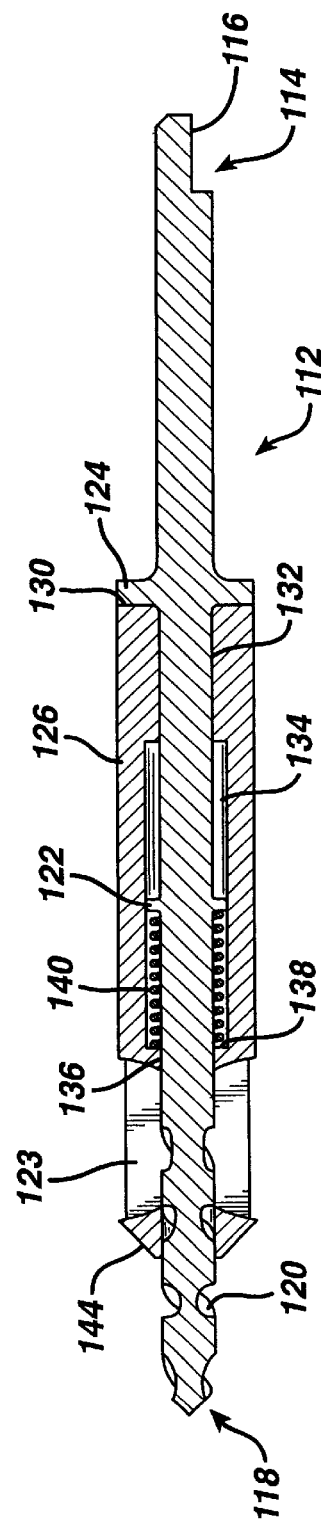
FIG. 12
FIG. 13

INSTRUMENT AND METHOD FOR APPLYING SURGICAL FASTENERS

Priority is claimed to Provisional Application Ser. No. 60/234,491 filing date Sep. 22, 2000.

FIELD OF THE INVENTION

The present invention relates to an apparatus and method for applying surgical fasteners, and in one particular aspect to such an apparatus and method for driving rivets to secure cranial plates.

BACKGROUND

It is known in the art to apply fasteners for attaching sutures, bone plates, and connective tissue. The fastener is inserted into a hole in a bone and generally through some application of force is caused to expand. One particular method for driving a fastener is disclosed in U.S. Pat. No. 5,398,861 by Green which discloses a spring loaded retractable piston and a pivotable trigger device for releasing the piston and allowing it to drive forward and drive home a fastener. One disadvantage of this device lies in the difficulty in grasping the device and firing the trigger simultaneously.

SUMMARY OF THE INVENTION

An instrument according to the present invention for applying a surgical fastener comprises an elongated body having proximal and distal ends. A piston is axially moveable within a bore within the body, the piston having a distal end adjacent the body distal end and a slit through the body to the bore, the slit extending a distance axially from the body distal end. The bore at the body distal end is sized to snugly receive a portion of the fastener therein and the slit allows the body to compressively hold this portion of the fastener. The inside diameter of the bore prior to cutting the slit is preferably about 0.0595 inches and the outside diameter of said portion of the fastener is about 0.0590 inches and the slit is about 0.014 inches wide. Preferably, the slit has a distal end at the body distal end, and an opposite proximal end, the proximal end of the slit opening into an aperture wider than the slit whereby to reduce stress on the body at the slit proximal end. Preferably, a spring urges the piston toward the body distal end and a releasable catch on the body restrains distal movement of the piston whereby release of the catch allows the spring to move the piston distally to impact and apply the surgical fastener.

A method according to the present invention provides for holding a surgical fastener within an instrument for applying the fastener. The method comprises the steps of: providing an instrument comprising an elongated body having proximal and distal ends, a piston axially moveable within a bore within the body, the piston having a distal end adjacent the body distal end, and a slit through the body to the bore, the slit extending a distance axially from the body distal end; and pushing a portion of the fastener into the bore at the body distal end, the body contracting about portion of the plug to hold the plug within the body. To apply the fastener the piston is moved distally to engage and thereby apply the fastener. Preferably, the fastener comprises a plurality of axially extending leaves and a cylindrical plug adjacent thereto and the method further comprising the step of pushing the plug with the piston between the leaves to spread the leaves and expand the fastener. Preferably, the fastener is formed of a bioabsorbable material.

BRIEF DESCRIPTION OF THE DRAWINGS

FIG. 12 is top plan view of a drill for drilling holes in a skull to receive the fastener of FIG. 4; and FIG. 13 is a sectional view taken along lines 13—13 of FIG. 12.

DETAILED DESCRIPTION

Figure 1:
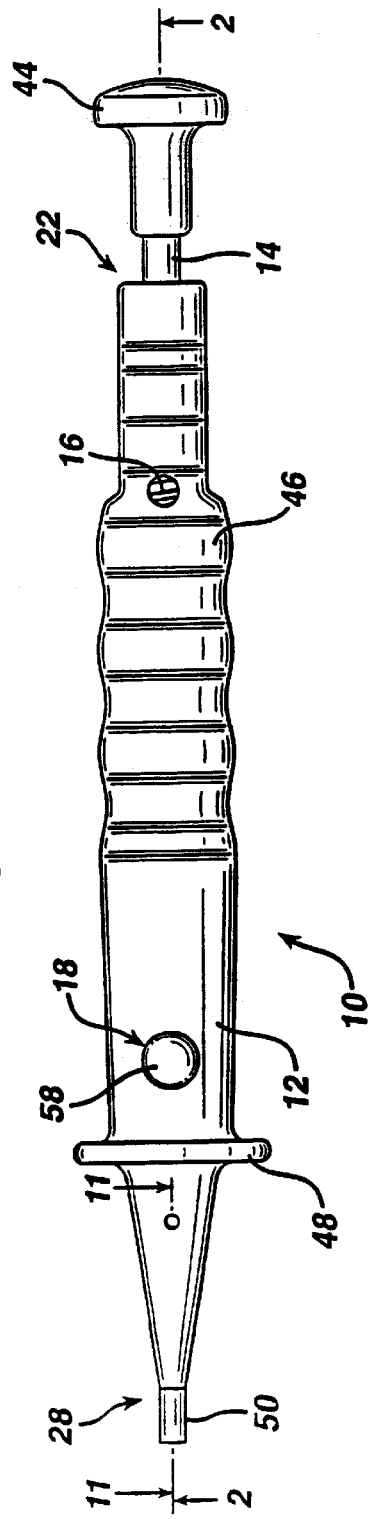
FIG. 1 is a top plan view of an instrument for applying surgical fasteners according to the present invention.
Figure 2:
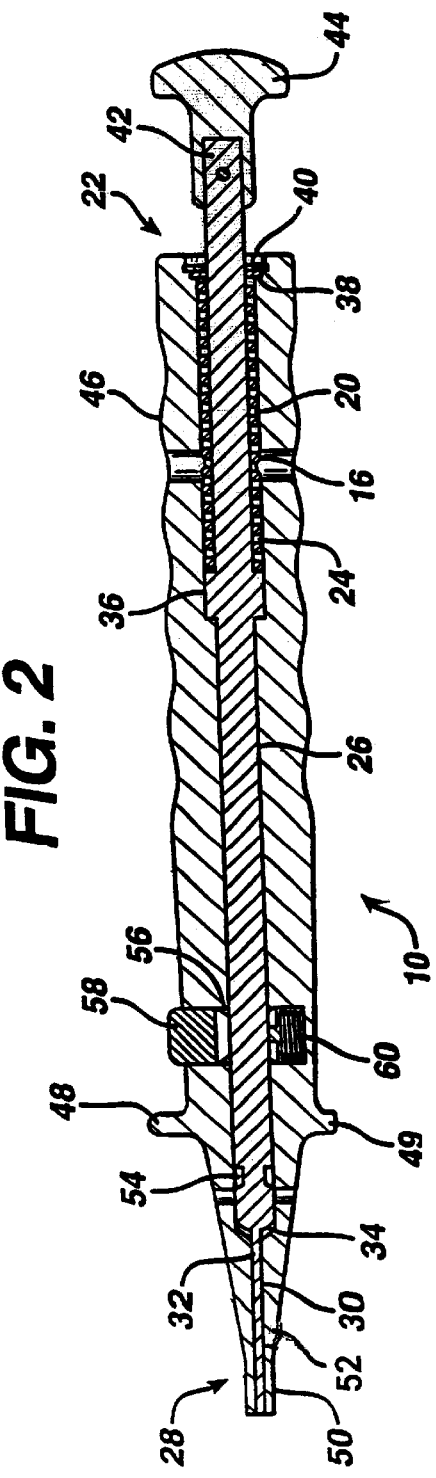
FIG. 2 is a section view taken along lines 2—2 of FIG. 1.

Referring now to the drawings, FIGS. 1 and 2 illustrate a rivet applier 10 according to the present invention. It comprises in general an elongated cylindrical body 12, a piston 14 restrained by a spring 16 and a release mechanism 18. An axial bore 20 passes through the body 12 and has varying diameters. At a proximal end 22 of the body 12 a first portion 24 of the bore 20 has a relatively large diameter to accommodate the spring 16 which is coiled about the piston 14 within the first portion 24. Intermediate portion 26 of the bore 20 has an intermediate diameter closely matched to the diameter of the piston 14.

At a distal end 28 of the body 12 a distal portion 30 of the bore 20 has a narrow diameter to accommodate a hardened setting pin 32 which projects axially from a distal end 34 of the piston 14. Preferably, the setting pin 32 is an integral part of the piston 14, but can alternatively be a separate piece affixed to the piston 14.

The spring 16 is caged between a flange or retaining clip 36 about the piston 14, and a washer 38 and retaining clip 40 at the body proximal end 22. The piston 14 passes outwardly of the body 12 through the washer 38 and retaining clip 14.

At a proximal end 42 of the piston 14 a handle 44 is provided for manual retraction of the piston 14. The proximal half of the body 12 is provided with flutes 46 for enhancing gripability and an axial flange 48 is provided near the body distal end 28 also to enhance gripability and maneuverability of the rivet applier 10. A flat 49 on the flange 48 inhibits rotation of the rivet applier 10, thereby reducing the likelihood that it will roll off of a surface upon which it is placed. The body distal end 28 tapers to a narrow tip 50 to allow more precise direction of the instrument 10. The set pin 32 is fixed within a coaxial bore 52 in the piston distal end 34.

Figure 3:
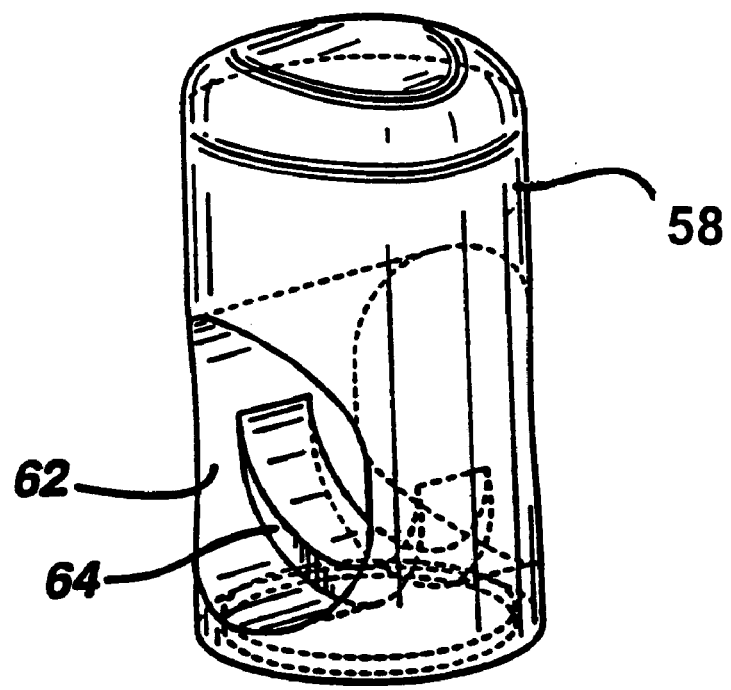
FIG. 3 is a perspective detail view of a release button for the instrument of FIG. 1.

A circumferencial groove 54 surrounds the piston 14 near its distal end 34. A radial bore 56 passes into the body 12 adjacent the groove 54 and extends beyond the bore 20 but does not completely penetrate the body 12. Turning also to FIG. 3 the release mechanism 18 comprises a release button 58 received within the bore 56 and a the coil spring 60 between an end of the bore 56 and the button 58 which biases the button outwardly of the bore 56. The button 58 has a radial bore 62 through which passes the piston 14. A radial flange 64 within the bore 62 is adapted to engage the circumferential groove 54 on the piston 14.

When the handle 44 is retracted, causing the piston 14 to retract proximally, the flange 64 rides over the surface of the piston 14 until it encounters the circumferential groove 54 into which the spring 60 causes the flange 64 to slip. This action locks the piston 14 in a retracted position as its distal motion is restrained by the abutment of the flange 64 and groove 54. Inward pressure applied to the button 58 causes the flange 64 to disengage from the circumferential groove 54 and allows the spring 16 to drive the piston 14 forward or distally. This causes the setting pin 32 to move distally to a position flush with the distal end of the body 12.

Figure 4:
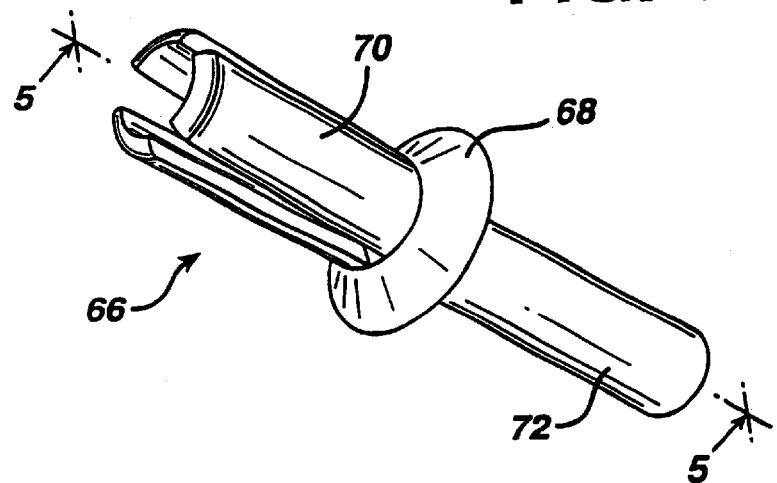
FIG. 4 is perspective view of a fastener for using in the instrument of FIG. 1.
Figure 5:
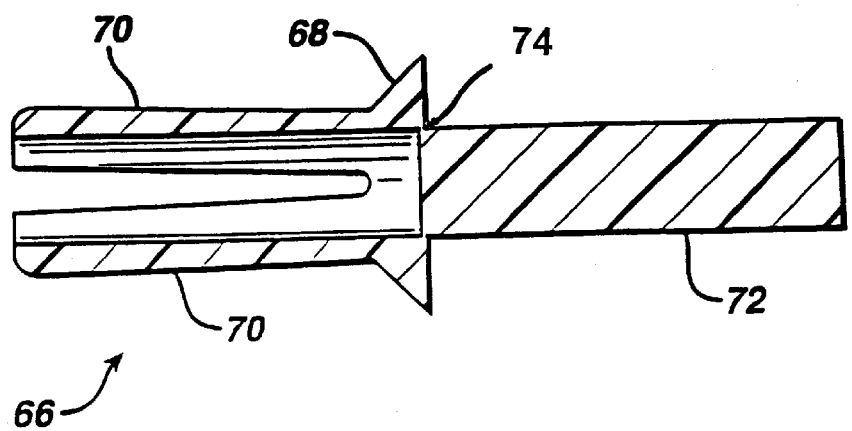
FIG. 5 is a section view taken along lines 5—5 of FIG. 4.

FIGS. 4 and 5 illustrate a rivet 66 for use with the instrument 10. The rivet 66 comprises a round head 68 from which extends axially 3 leaves 70. A cylindrical plug 72 extends axially from the head 68 in the opposite direction and is frangible connected to the head 68 through a frangible connection 74. The surfaces of the leaves 70 are curved so that the combination of the three leaves 70 provides an overall tubular configuration. Application of force in the axial direction applied to the plug 72 breaks its frangible connection 74 with the head 68 and allows it to drive axially into a position between the leaves 70 thus causing the leaves 70 to spread.

Figure 6:
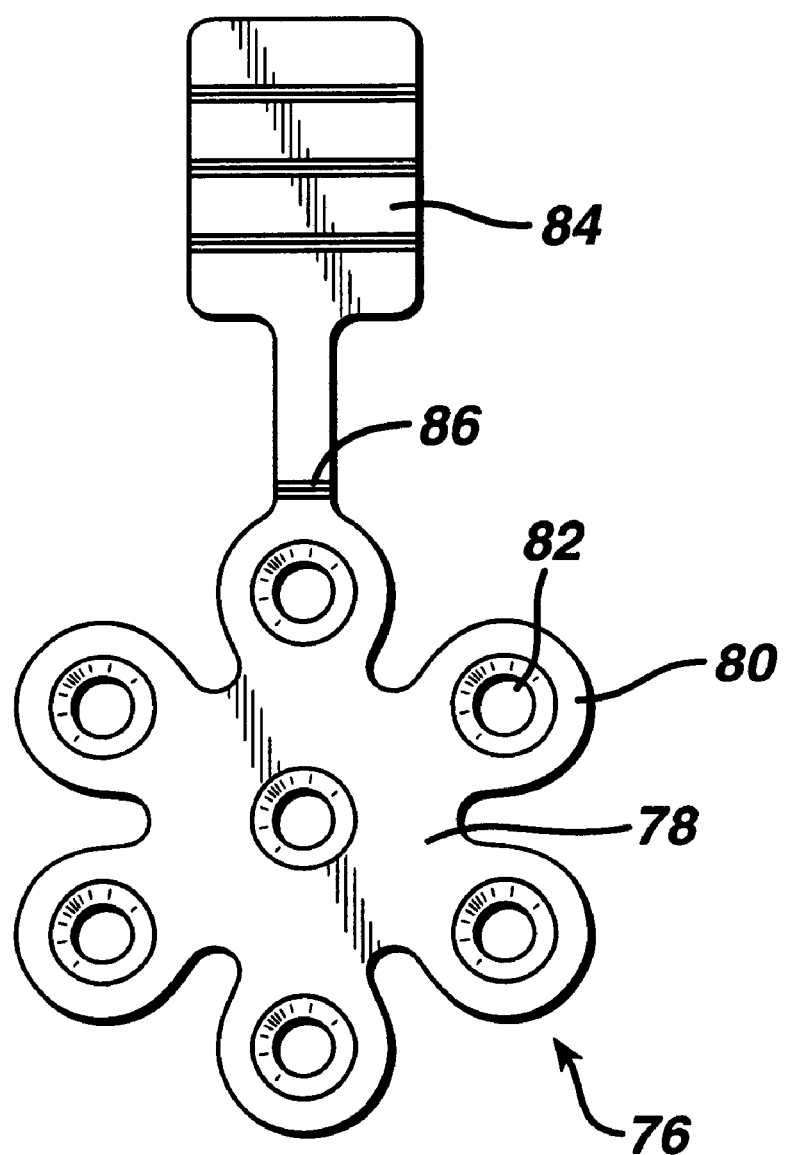
FIG. 6 is a top plan view of a plate to be applied using the fastener of FIG. 4.
Figure 7:
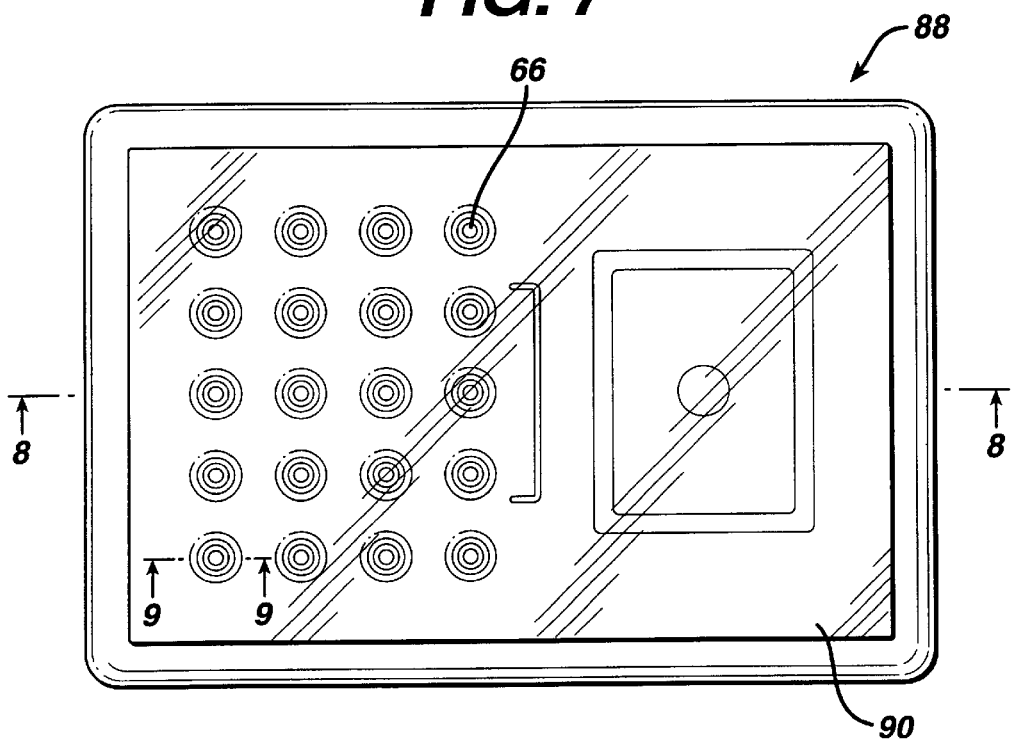
FIG. 7 is a top plan view of a tray holding a plurality of the fasteners of FIG. 4.
Figure 8:
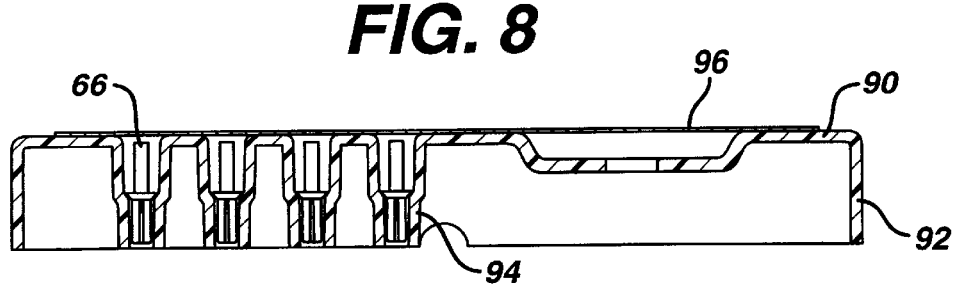
FIG. 8 is a sectional view taken along lines 8—8 of FIG. 7.
Figure 9:
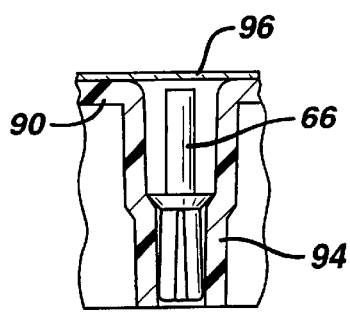
FIG. 9 is a detail sectional view taken along lines 9—9 of FIG. 7.
Figure 10:
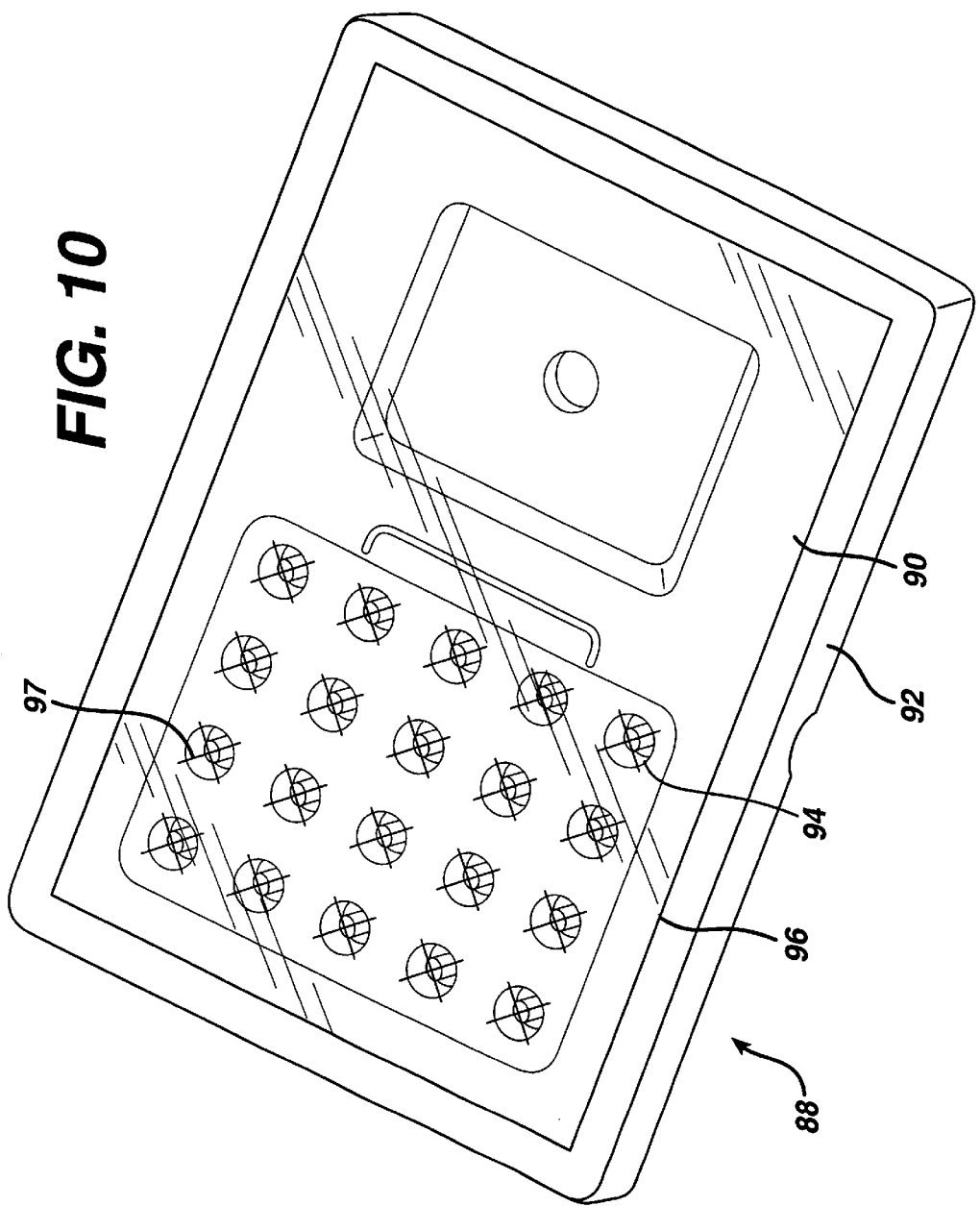
FIG. 10 is a perspective view of the tray of FIG. 7.

FIG. 6 shows a cranial plate 76 for placement on a skull of an patient, either human or animal (not shown). It comprises a flat planar body 78 having a plurality of circular extensions 80 therefrom, each of which has a countersunk bore 82 therethrough. A tag 84 extends from the plate 76 and serves several functions. The tag 84 may contain model number, size, material, date and other pertinent information as well as showing which side of the plate 76 is to face upwards away from the patient's skull (not shown). It also provides a purchase location for a user's hand to hold and manipulate the plate 76 during placement. A frangible connection 86 between the tag 84 and the remainder of the plate 76 allows easy removal of the tag 84 from the plate 76 after placement of the plate 76. Many other configurations of plates will be apparent to those of skill in the art.

Turning to FIGS. 7 to 10, the rivets 66 are disposed for use in a tray 88. The tray 88 comprises a base 90 having a downwardly extending peripheral wall 92 and a plurality of wells 94 therein. Preferably, the wells 94 penetrate the base 90. A plurality of the rivets 66 reside within the plurality of the wells 94 with their plugs 72 facing upwardly out of the wells 94. A film cover 96 adheres to the base 90 over at least the area of the base 90 comprising the wells 92 to hold the rivets 66 within the wells 92. The film cover 96 preferably has slits 97, scorings or some other weakness at each of the wells 92 to allow access to the rivets 66 through the film cover 96 by the instrument 10 (not shown in FIGS. 8 to 10), although a suitable material allowing access therethrough without slits or the like may be employed.

Figure 11:
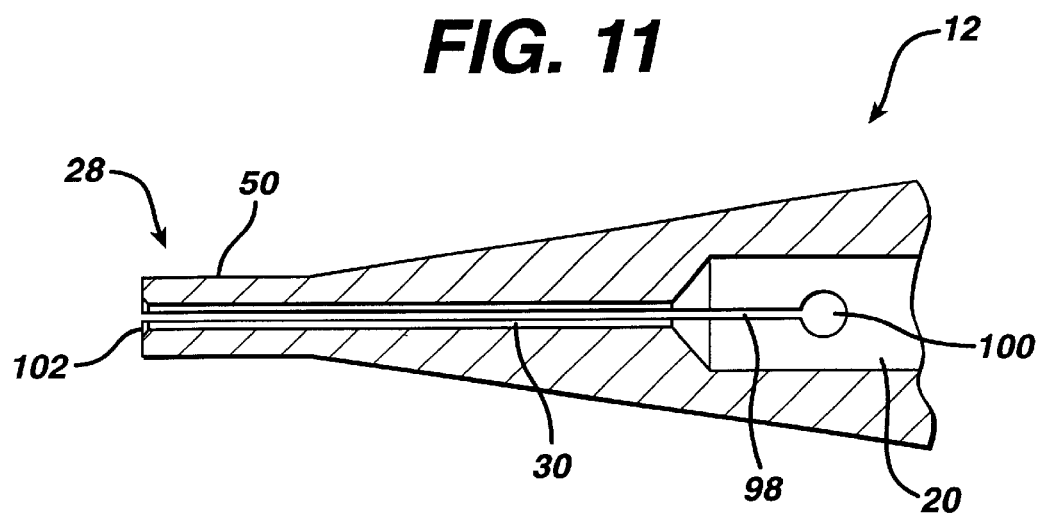
FIG. 11 is a sectional view taken along lines 11—11 of FIG. 1.

FIG. 11 illustrates the distal tip 50 of the instrument body 12. It comprises at least one axial slit 98 extending proximally from the distal end 28 and terminating in an aperture 100. A chamfer 102 is also provided at the distal end of the bore 20. In one preferred embodiment, the plugs 72 of the rivets 66 (FIG. 4) have an outside diameter of 0.0590 inches (1.50 mm), the bore distal portion 30 has an inside diameter of 0.0595 inches (15.1 mm) and the outside diameter of the tip 50 is 0.140 inches (3.56 mm). The slit 98 allows the material of the tip 50 to contract slightly thus reducing the effective internal diameter of the bore distal portion 30 and the aperture 100 reduces stress risers during flexing.

Preferably the rivet 66 and plate 76 are formed of a bioabsorbable material such as a polylactide, such as an 85:15 (mol/mol) poly(lactide-co-glycolide) copolymer. More preferably, the rivet 66 is formed of PLLA and the plates are formed of 50/50 D, LPLA blended with 95/5 PCL/PDO in a 91:9 ratio as more fully described in U.S. Pat. Nos. 5,641,501 and 5,705,181, incorporated herein by reference. Preferably the instrument body 12 is formed of a sturdy material such as stainless steel, however, many other materials, including polymers, would be suitable. Preferably, the instrument body 12 weighs considerably more than the piston 14 so as to minimize kick-back as the piston 14 is released. The setting pin 32, and especially if the setting pin 32 and piston 14 are integral, is preferably formed of a hardened steel or stainless steel, but of course many other hardy materials would be suitable for such service. The tray 88 preferably is formed of a suitable polymer, but can also be formed of other materials.

To use the instrument 10, a user grasps the handle 42 and retracts the piston 14 until the flange 64 of the release mechanism 18 engages the annular groove 54 of the piston 14 and holds the piston 14 in a retracted position. The tip 50 of the instrument 10 is inserted through one of the slits 97 to capture the plug 72 of one of the rivets 66 within the bore distal portion 30. The chamfer 102 eases entry of the plug 72 into the bore distal portion 30 and contraction of the tip 50 due to the slit 98 helps the tip 50 grip the plug 72. The rivet 66 is then placed through one of the plate apertures 82 and into a hole in the skull (not shown) and the rivet applier is held thereagainst with some force, say 2 pounds force. Pressing the button 58 releases the engagement of the piston 14 and flange 64 allowing the setting pin 32 to move distally to push against the plug 72 breaking its frangible connection to the head 68 and driving it between the leaves 70 thereby spreading the leaves and setting the rivet 66.

FIGS. 12 and 13 illustrate a bone drill 110 which provides a simple and elegant solution to the problem of centering and boring holes in a patient's skull into which the rivets 66 (not shown in FIG. 12) are received when applying the cranial plate 76 (also not shown in FIG. 12). The drill 110 comprises an elongated drill bit 112 having a proximal end 114 with an attachment surface 116 for attachment to a drill chuck (not shown). Any appropriate attachment surface can be substituted therefor. For instance, a two-piece cap (not shown) can be employed which fits into the tube instead of using a right and left half as shown. A distal end 118 of the drill bit 112 carries helical cutting edges 120, but other forms of cutting surfaces as appropriate can be substituted therefor. A first radial flange 122 extends radially outwardly from the drill bit 112 and a second larger radial flange 124 extends radially outwardly from the drill bit 112 proximal of the first radial flange 122. A pair of windows it 123 allow debris from the drilling to exit the drill 110 and are arranged so as to release the debris before it can reach and possibly interfere with operation of the spring 140.

A tubular housing 126 having an axial bore 128 therethrough coaxially receives the drill bit 112 through the axial bore 128. A proximal end 130 of the housing 126 abuts the second radial flange 124 and thereby limits distal movement of the drill bit 112 through the housing 126. A first diameter 132 of the bore 128 at the housing proximal end 130 closely matches the diameter of the drill bit 112 for sliding engagement. A central diameter 134 of the bore 128 closely matches the diameter of the first radial flange 122 for sliding engagement. A distal diameter 136 of the bore 128 closely matches the diameter of the drill bit 112 for sliding engagement, and the change in diameter of the bore 128 between the central diameter 134 and distal diameter 136 forms a radial abutment 138. A coil spring 140 encircles the drill bit 112 and operates between the abutment 138 and the first radial flange 122 to urge the housing distally along the drill bit 112.

A distal end 142 of the housing 126 carries a chamfer 144 of matching angle to the chamfer of the holes 82 in the cranial plate 76 (see FIG. 6). By pressing the distal end 142 into the chamfered hold 82 the drill bit 112 is centered within the hole 82 allowing accurate drilling. Abutment of the second radial flange 124 and the housing proximal end 130 limits travel of the drill bit 112 out of the housing 126 and thus limits the depth of a hole created by the drill bit 112.

While the invention has been described with regard to a particular embodiment thereof, those skilled in the art will understand, of course, that the invention is not limited thereto since modifications can be made by those skilled in the art, particularly in light of the foregoing teachings. Reasonable variation and modification are possible within the foregoing disclosure of the invention without the departing from the spirit of the invention.

What is claimed is:

1. An instrument for applying a surgical fastener, the instrument comprising:

an elongated body having proximal and distal ends;

a piston axially moveable within a bore within the body, the piston having a distal end adjacent the body distal end; and a slit through the body to the bore, the slit extending a distance axially from the body distal end, the slit has a distal end at the body distal end, and an opposite proximal end, the proximal end of the slit opening into an aperture wider than the slit whereby to reduce stress on the body at the slit proximal end;

wherein the bore at the body distal end is sized to snugly receive a portion of the fastener therein, the slit allowing the body to compressively hold said portion of the fastener.

2. An instrument according to claim 1 wherein the inside diameter of the bore prior to cutting the slit is about 0.0595 inches and the slit is about 0.014 inches wide.

3. An instrument according to claim 1 and further comprising a spring urging the piston toward the body distal end and a releasable catch on the body for restraining distal movement of the piston whereby release of the catch allows the spring to move the piston distally to impact and apply the surgical fastener.

4. A method of holding a surgical fastener within an instrument for applying said fastener, the method comprising the steps of:

providing an instrument comprising an elongated body having proximal and distal ends, a piston axially moveable within a bore within the body, the piston having a distal end adjacent the body distal end, and a slit through the body to the bore, the slit extending a distance axially from the body distal end, the slit has a distal end at the body distal end, and an opposite proximal end, the proximal end of the slit opening into an aperture wider than the slit whereby to reduce stress on the body at the slit proximal end; and pushing a portion of the fastener into the bore at the body distal end, the body contracting about portion of the plug to hold the plug within the body.

5. The method of claim 4 and further comprising moving the piston distally to engage and apply the fastener.

6. The method of claim 5 wherein the fastener comprises a plurality of axially extending leaves and a cylindrical plug adjacent thereto and the method further comprising the step of pushing the plug with the piston between the leaves to spread the leaves and expand the fastener.

7. The method of claim 6 wherein the fastener is formed of a bioabsorbable material.

8. The method of claim 5 further comprising the step of restraining distal movement of the piston with a releasable catch and urging the piston distally with a spring and then releasing the catch to drive the piston distally with the spring.

* * * * *